US010105447B2

United States Patent
Bledsoe et al.

(10) Patent No.: US 10,105,447 B2
(45) Date of Patent: Oct. 23, 2018

(54) METHOD OF TREATING OBESITY IN A COMPANION ANIMAL COMPRISING ADMINISTERING A MODIFIED CANINE LEPTIN POLYPEPTIDE

(71) Applicants: ELANCO US INC., Greenfield, IN (US); Ambrx, Inc., La Jolla, CA (US)

(72) Inventors: Michael Bledsoe, San Diego, CA (US); Peter Connor Canning, Indianapolis, IN (US); Michael Deguzman, La Jolla, CA (US); Nick Knudsen, La Jolla, CA (US); Ianina Valenta, La Jolla, CA (US)

(73) Assignees: ELANCO US INC., Greenfield, IN (US); AMBRX, INC., La Jolla, CA (US)

( * ) Notice: Subject to any disclaimer, the term of this patent is extended or adjusted under 35 U.S.C. 154(b) by 0 days.

(21) Appl. No.: 14/765,931

(22) PCT Filed: Mar. 12, 2014

(86) PCT No.: PCT/US2014/024706
§ 371 (c)(1),
(2) Date: Aug. 5, 2015

(87) PCT Pub. No.: WO2014/165189
PCT Pub. Date: Oct. 9, 2014

(65) Prior Publication Data
US 2015/0366983 A1 Dec. 24, 2015

Related U.S. Application Data

(60) Provisional application No. 61/779,337, filed on Mar. 13, 2013.

(51) Int. Cl.
*A61K 38/22* (2006.01)
*A61K 47/48* (2006.01)
*C07K 14/575* (2006.01)
*A61K 47/60* (2017.01)

(52) U.S. Cl.
CPC .... *A61K 47/48215* (2013.01); *A61K 38/2264* (2013.01); *A61K 47/60* (2017.08); *C07K 14/5759* (2013.01)

(58) Field of Classification Search
CPC ................ A61K 38/2264; A61K 47/48215
See application file for complete search history.

(56) References Cited

U.S. PATENT DOCUMENTS

| | | | |
|---|---|---|---|
| 2012/0149636 A1 | 6/2012 | Kraynov et al. | |
| 2012/0164130 A1* | 6/2012 | Brooks | C12Y 304/2102 424/94.64 |

FOREIGN PATENT DOCUMENTS

| | | | |
|---|---|---|---|
| CN | 1217023 A | 5/1999 | |
| CN | 101113175 A | 1/2008 | |
| CN | 101939443 A | 1/2011 | |
| JP | 2000-513564 A | 10/2000 | |
| JP | 2000279171 A | 10/2000 | |
| JP | 2006507814 A | 3/2006 | |
| JP | 2009-216487 A | 9/2009 | |
| JP | 2011-526780 A | 10/2011 | |
| JP | 2013-500726 A | 1/2013 | |
| KR | 10-1999-0087392 | 12/1999 | |
| WO | WO-97/32022 A2 | 9/1997 | |
| WO | WO-01/21647 A2 | 3/2001 | |
| WO | WO-2009/100255 A2 | 8/2009 | |
| WO | WO-2011-014890 A1 | 2/2011 | |

OTHER PUBLICATIONS

Cho et al., PNAS 2011, 108: 9060-9065.*
LeBel et al. Obesity Research; 1999, 7:577-585.*
International Search Report and Written Opinion dated Oct. 7, 2014 for PCT/US2014/024706.
Written Opinion of the International Searching Authority dated Oct. 7, 2014 for PCT/US2014/024706.
Office Action dated May 31, 2016 in Japanese Patent Application No. 2016-501613 (4 pages) with an English Translation (4 pages).
Patent Examination Report No. 1 dated Dec. 2, 2015 in Australian Patent Application No. 2014248617.
Canadian Application No. 2,901,928—Office Action dated Jun. 17, 2016 including Examination Report dated Jun. 16, 2016.
Leptin precursor [Canis lupus familiaris], NCBI Reference Sequence No. 001003070.1, Feb. 22, 2013.
KIPO's Notice of Preliminary Rejection dated Jun. 2, 2017 in Korean Patent Application No. 10-2015-7027899 (5 pages) with an English translation (3 pages).
English translation of the First Office Action dated Jun. 1, 2017 in Chinese Patent Application No. 201480014677.9.

* cited by examiner

*Primary Examiner* — Gyan Chandra
(74) *Attorney, Agent, or Firm* — McAndrews, Held & Malloy, Ltd.

(57) ABSTRACT

Modified canine leptin polypeptides and formulations and uses thereof, are provided including polyethylene glycol (PEG) modified canine leptin polypeptides, wherein the PEG moiety is covalently attached to a para-acetyl-phenylalanine (pAF) residue of the polypeptide, and related compositions and methods useful in treating companion animal obesity and other leptin-related disorders.

5 Claims, No Drawings

Specification includes a Sequence Listing.

METHOD OF TREATING OBESITY IN A COMPANION ANIMAL COMPRISING ADMINISTERING A MODIFIED CANINE LEPTIN POLYPEPTIDE

REFERENCE TO RELATED APPLICATIONS

This application is a 371 national stage of PCT/US2014/024706 filed Mar. 12, 2014, and claims the benefit of U.S. Provisional Application No. 61/779,337, filed Mar. 13, 2013.

SEQUENCE LISTING

The instant application contains a Sequence Listing which has been submitted electronically in ASCII format and is hereby incorporated by reference in its entirety. Said ASCII copy, created on Mar. 7, 2014, is named 204257-0016-WO-00(509186)_SL.txt and is 2,597 bytes in size.

The present invention relates to a polyethylene glycol (PEG) modified canine leptin polypeptide and related compositions and methods useful in treating companion animal obesity and other leptin-related disorders.

Leptin is a neurohormone that acts in the hypothalamus to regulate energy balance and food intake. Much has been written about the problems associated with leptin and its receptor for humans (US2012/0149,636), but companion animals also suffer from leptin-related disorders. Of particular note are companion animals, such as canines, which experience leptin-disorders, such as obesity. While administering exogenous leptin as a therapy is known in humans, it is hampered by several problems, not the least of which is the failure to provide long lasting effect. Thus, efforts to find better alternatives are ongoing and these efforts include finding safer, longer lasting, and more potent compounds for humans as well as companion animals.

The present invention provides a compound comprising a polypeptide of SEQ ID NO: 1 and a polyethylene glycol (PEG) moiety, wherein the PEG moiety is covalently attached to a para-acetyl-phenylalanine (pAF) residue of the polypeptide of SEQ ID NO:1.

The present invention also provides a method of treating obesity in companion animals comprising administering to an animal in need thereof an effective amount of a compound according to the present invention.

The present invention also provides a method of preventing obesity in companion animals comprising administering to an animal in need thereof an effective amount of a compound according to the present invention.

The present invention also provides a compound according to the present invention for use in therapy.

The present invention also provides a compound according to the present invention for use in the treatment of obesity.

The present invention also provides a compound according to the present invention for use in the prevention of obesity.

The present invention also provides a composition comprising the compound according to the present invention and one or more carriers, diluents or excipients.

The amino acid sequence of the polypeptide is:

wherein Xaa is para-acetyl-phenylalanine (pAF) (SEQ ID NO:1).

An example of a DNA molecule that encodes the amino acid sequence of SEQ ID NO:1 is:

```
                                        (SEQ ID NO: 2)
atg gtt cca att cga aag gtt caa gat gat acg aag aca ctg atc aag act atc gtg gcg cgc atc aac gat att tcg cat acc cag tca gtc tcg tcg aaa caa cgt gtg gat ggc tta gat ttt att cca ggg ctg caa ccg gta ctg tct ctg agc cgt atg gac caa act ctg gcc atc tac cag caa atc ctt aac tct ctg cat tct cgc aat gtg gtg caa atc tcg aac gat ctt gag aac ttg cgt gac ctg tta cat ctg tta gcc tca agc aaa tca tgc ccg ctg ccg cgt gca cgt ggc ctt gaa acg ttt gaa agt ttg tag ggt gtc ttg gaa gcg agt ctt tat tcc acc gaa gtc gtc gcc ctg aac cgc ctg cag gcc gca ctt caa gac atg ctt cgc cgt ctg gat ctc agt ccg ggt tgc.
```

As a result of processing, the first methionine may be cleaved and therefore not present in the mature polypeptide, resulting in a mixture of SEQ ID NO 1 with and without the first methionine cleaved. Preferrably, the final mixture contains less than ten (10) percent or less than five (5) percent of SEQ ID NO 1, wherein the first methionine is cleaved. Most preferably, the final mixture contains 2 percent or less of SEQ ID NO 1, wherein the first methionine is cleaved.

Non naturally occurring amino acids are known in the art. One particular non-naturally occurring amino acid is known as para-acetyl-phenylalanine (pAF). The polypeptides of the invention can be generated in vivo using modified tRNA and tRNA synthetases to incorporate pAF in response to an amber stop codon in the gene encoding the polypeptide as described in US2012/0149,636. An expression plasmid or vector that directs the expression of the polypeptide of SEQ ID NO:1 is transfected into a modified E. coli K-12 W3110 strain. The E. coli K-12 host strain is a W3110 derivative which is modified to contain the plasmid containing a DNA sequence with an amber stop codon (TAG) at the site where the pAF is incorporated, Xaa at position 112 of SEQ ID NO:1. The plasmid also contains genes for a modified tyrosyl tRNA and aminoacyl-tRNA synthetase (aa-RS) pair derived from Methanococcus jannaschii DSM 2661 (MjTyr-CUA tRNA and Tyr-RS). This pair is modified and genetically selected to incorporate pAF in response to the amber stop codon.

PEG moieties used in the present invention have average molecular weights between 1 kDa and 100 kDa, or between 1 kDa and 50 kDa, or between 20 kDa and 50 kDa. A preferred PEG moiety has a molecular weight of about 20 kDa. Another preferred PEG moiety has a molecular weight of about 30 kDa. Yet another preferred PEG moiety has a molecular weight of about 40 kDa. PEG is used to encom-

```
MVPIRKVQDD TKTLIKTIVA RINDISHTQS VSSKQRVAGL DFIPGLQPVL  50

SLSRMDQTLA IYQQILNSLH SRNVVQISND LENLRDLLHL LASSKSCPLP  100

RARGLETFES LXaaGVLEASLY STEVVALNRL QAALQDMLRR LDLSPGC    147
``` pass both linear and branched polymers. Most PEGs are commercially available. Preferably the PEG is a 30 kDa PEG (α-Methyl-ω-amimooxyethylcarbamyl, polyoxyethylene.

Animal refers to companion animals such as dogs and cats.

The compounds of the invention are useful in treating a companion animal having a disorder modulated by leptin. Such disorders include obesity and obesity-induced or obesity-related disorders. Obesity is a condition in which there is an excess of adipose tissue in proportion to lean tissue. Treatment of obesity and obesity-induced or obesity-related disorders refers to the administration of the compound of the present invention to reduce food intake, to preferentially reduce the amount of adipose tissue, and reduce body weight of an obese companion animal. One outcome of treatment may be reducing the body weight of an obese companion animal relative to that animal's body weight before the administration of the compounds of the present invention. The treatment may suitably result in a reduction in food or calorie intake by the animal, including a reduction in total food intake, and in weight reduction in animals in need thereof. Prevention of obesity and obesity-related disorders refers to the administration of the polypeptides of the present invention to reduce food intake, to reduce body weight, or to maintain the body weight of a animal at risk of obesity. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a animal at risk of obesity.

The compounds of the present invention may be combined with, or employ, one or more other active ingredients in therapies for, and for treating, an animal who has a disorder modulated by canin leptin.

A compound of the present invention can be incorporated into a composition suitable for administration to an animal. Such compositions are designed to be appropriate for the selected mode of administration, and acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., *Remington, The Science and Practice of Pharmacy*, 19$^{th}$ Edition, Gennaro, Ed., Mack Publishing Co., Easton, Pa. 1995 which provides a compendium of formulation techniques as are generally known to practitioners. Suitable carriers for compositions include any material which, when combined with a compound of the invention, retains the compound's activity and is non-reactive with the animal's immune system. A composition of the present invention comprises a compound and one or more pharmaceutically acceptable carriers, diluents or excipients.

A composition comprising a compound of the present invention can be administered to a animal at risk for or exhibiting diseases or disorders as described herein using standard administration techniques. A composition of the invention contains an effective amount of a compound of the invention. An effective amount refers to an amount (at dosages and for periods of time and for the means of administration) to achieve the desired therapeutic result. An effective amount of the compound may vary according to factors such as the disease state, age, sex, and weight of the animal, and the ability of the compound to elicit a desired response in the animal. An effective amount is also one in which any toxic or detrimental effect of the compound, are outweighed by the therapeutically beneficial effects. An effective amount can be approximately 2% of the animal's initial bodyweight per week until the animal achieves the desired bodyweight as determined by the veterinarian and client. An effective amount/dose can be between about 0.1 to about 10 mg/kg weight of the animal per week, administered for example by subcutaneous injection. An effective amount/dose can be 1 mg/kg administered by SC injection once per week.

EXAMPLE 1

The polypeptide of SEQ ID NO:1 is obtained essentially as described in US2012/0149,636. The polypeptide of SEQ ID NO:1 is formulated to 4 mg/mL in 20 mM Tris pH 4.0; 2 M urea; and 50 mM methionine. To this formulated polypeptide, 30K PEG (α-Methyl-ω-amimooxyethylcarbamyl, polyoxyethylene, Sunbright ME-300CA, NOF, Japan) is added tat a 10:1 PEG to polypeptide molar ratio. The polypeptide and PEG are mixed gently and conjugation is allowed to proceed for 48-72 hours at 28° C. The PEGylated polypeptide is then purified by routine cation exchange chromatography and formulated to 1 mg/ML in PBS (phosphate buffered saline) 7.4 with 4% trehalose. This process results in a mixture which contains between 1-2% of SEQ ID NO: 1, wherein the first methionine is cleaved off.

In Vitro Biological Data

HEK 293 cells are stably transfected with both the luciferase reporter gene under control of a STAT3 response element and the OB-Rb (leptin receptor), which is expressed on the cell surface. Leptin binds to the leptin receptor and activates STAT3 homodimers and STAT3/STAT1 heterodimers, which interact and bind with the STAT3 sequence response element. This interaction drives expression of the luciferase gene and stimulates cells to produce luminescence. The amount of luminescence is proportional to the activity of the compound. The biological activity is based on the EC50 of a 4-PL sigmoidal curve.

Day One

Cells are seeded into a 96-well plate at 20,000 cells/well and placed in a 37° C., 5% CO2 incubator for 24-30 hours.

Day Two

The starting concentration for wild type (WT) canine leptin and the PEGylated polypeptide of Example 1 is 1200 ng/mL. From that, 400 uL volume is taken from each sample and 4× serial dilutions are made across the rows of the dilution block. First, 300 uL/well of assay medium is added to Col 2-11. Then 100 uL is transferred from Col 1 to Col 2, mixed carefully and slowly (without bubbling) 8-10 times, and then continued transferring 100 uL from Col 2 to Col 3 and repeating until reaching Col 11. Leave Col 12 as un-stimulated control well. Cells are then stimulated with the serial dilutions of the wild type (WT) canine leptin and the PEGylated polypeptide of Example 1. The cells are taken out of the incubator and the medium is carefully aspirated from each well. Then 100 μL/well of the serially diluted WT and PEGylated polypeptide is transferred from the deep-well dilution block to the cells in the 96-well assay plates. Duplicate samples are then created for WT and PEGylated polypeptide tested horizontally across the next available row. Plates are incubated in a 37° C., 5% $CO_2$ incubator for 16-18 hours. The plate format with final concentrations in ng/mL is shown below.

|  | [ng/mL] | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| WT cLeptin | 1200 | 300 | 75 | 19 | 4.68 | 1.17 | 0.29 | 0.073 | 0.018 | 0.0046 | 0.0011 | 0 |
| WT cLeptin | 1200 | 300 | 75 | 19 | 4.68 | 1.17 | 0.29 | 0.073 | 0.018 | 0.0046 | 0.0011 | 0 |
| Example 1 | 1200 | 300 | 75 | 19 | 4.68 | 1.17 | 0.29 | 0.073 | 0.018 | 0.0046 | 0.0011 | 0 |
| Example 1 | 1200 | 300 | 75 | 19 | 4.68 | 1.17 | 0.29 | 0.073 | 0.018 | 0.0046 | 0.0011 | 0 |

Day Three

On day three, a substrate is prepared and added to the cells and they are then measured by a Luminometer. Approximately 1-2 hours before the plate is read, one set of Steady-Glo (Promega) reagents is thawed including: one vial of Steady-Glo lyophilized Luciferase Assay Substrate and one vial of Steady-Glo Luciverase Assay buffer per assay plate at room temperature. The entire contents of the luciverase assay buffer (~10.5 mL) are pipetted into the lyophilized luciferase substrate. 100 μL/well of the reconstituted luciferase substrate is added to each well of the assay plate and the assay plate is covered with aluminum foil and incubated at room temperature for 45-60 minutes on a plate shaker set at 450 to 600 rpm. The plate is then read on a Tecan GENiosPRO plate reader with integration time set to 250 msec. The data is then entered into Excel and an EC50 determination on SigmaPlot Application is carried out and the fold loss activity relative to the WT Leptin and percent relative potency determinations are also carried out. Fold loss activity relative to wild type canine leptin is determined to be the [EC50 of the sample] divided by the [EC50 of wild type leptin]; the % relative potency of leptin proteins to reference standard is calculated by dividing the EC50 of reference standard by the EC50 values of leptin proteins and multiplying by 100. For instance, the % Relative Potency is calculated as the [EC50 of referenced standard] divided by the [EC50 of the sample]×100. The following table shows WT and PEGylated polypeptide of Example 1 analyzed using these methods.

TABLE 1

| Molecule | Exp. 1 (EC50) | Exp. 2 (EC50) | AVG EC50 |
|---|---|---|---|
| WT Canine Leptin (Ray Biotech) | 1504 | 1954 | 1729 |
| WT Human Leptin (Ambrx) | 2052 | 3589 | 2820 |
| Example 1 | 2183 | 2679 | 2431 |

The results show that the PEGylated polypeptide of Example 1 is active in vitro.

In Vivo Biological Data

The objective of this study is to evaluate the impact of the PEGylated polypeptide of Example 1 upon bodyweight, body composition, and feeding behavior in obese male and female dogs. The PEGylated polypeptide of Example 1 formulated at 5.1 mg/ml in phosphate buffered saline with a pH of 7.4 and 4% (w/v) trehalose.

Eighteen (18) dogs all over one (1) year old are used: nine (9) intact male and nine (9) intact female beagles. The dogs are obese, weighing approximately 12 to 18 kg (26.4 to 39.6 lbs). During the first four weeks of the acclimation period, (or until the desired starting weight is achieved), dogs are fed a laboratory a high fat (approx. 45%) dry food that meets or exceeds the nutritional requirements for maintenance and health. All dogs are fed ad libitum during this portion of the acclimation period to facilitate weight gain. During the last two weeks of the acclimation period and for the remainder of the study, all dogs are fed a commercial normal fat (approx. 12%) dry dog food, in order to reduce endogenous leptin levels and restore leptin sensitivity. Dogs in treatment groups 1 and 2 continue to be provided with food ad libitum throughout the remainder of the study. Animals in treatment group 3 are fed twice per day according to the label instructions for the diet. Animals are allowed ad libitum access to water via bowls or an automatic watering system contained in each cage. No other concomitant medications are administered during the course of the study.

This study is conducted as a randomized block design within each gender. Dogs are randomly assigned to pens. Animals are blocked by baseline (Day −14) bodyweights within each gender. There are three blocks with three males and three blocks with three females. Block one of males consist of the 3 males with lowest bodyweights and block one of females will consist of the 3 females with lowest bodyweights. The second blocks within each gender consist of the 3 males and 3 females with the next lowest bodyweights. The final block within each gender contains the 3 males and 3 females with the highest bodyweights.

The following table displays the treatments, dose regimens, and numbers of animals employed.

TABLE 2

| Treatment | Dose Regimen | # of Animals |
|---|---|---|
| 1) Negative Controls treated with sterile saline, fed ad libitum | SIDx5 Q7 Days | 6 animals (3M/3F) |
| 2) Treated with compound of Example 1 - 1 mg/kg, fed ad libitum | SIDx5 Q7 Days | 6 animals (3M/3F) |
| 3) Treated with compound of Example 1 - 1 mg/kg, fed twice daily | SIDx5 Q7 Days | 6 animals (3M/3F) |

Animals are divided into two gender groups of nine animals. Within each gender group, animals are ranked lowest to highest based on Day −14 bodyweights. Animals in each gender group are divided into blocks of three animals based on increasing baseline bodyweights. Animals are randomly assigned to pen locations using a randomization table provided by the sponsor.

The control and treated groups are administered via subcutaneous injection on Days 0, 7, 14, 21, 28. Serum samples (approximately 2-3 ml) are obtained prior to enrollment in the study on Day −14 prior to switching the animals to the low fat ration in order to acclimate the dogs to the bleeding procedure and to establish baseline endogenous leptin levels. The following table provides the circulating leptin level at days −14 and −1.

TABLE 3

| Treatment/Feeding Regimen | Day −14 [Leptin] | Day −1 [Leptin] |
|---|---|---|
| 1) Negative Controls treated with sterile saline, fed ad libitum | 9.9 ng/ml | 3.4 ng/ml |
| 2) Treated with compound of Example 1 - 1 mg/kg, fed ad libitum | 10.7 ng/ml | 3.7 ng/ml) |
| 3) Treated with compound of Example 1 - 1 mg/kg, fed twice daily | 7.6 ng/ml | 3.8 ng/ml |

Animals in all three treatment groups are subjected to DEXA (dual energy x-ray absorptiometry) scans on Day −1, Day 21 and Day 42 (the final study day) to determine the percentages of lean versus adipose tissue.

Daily feed consumption are recorded for animals enrolled in treatment groups 1 and 2 on Days −7 through 42 at approximately the same time each.

Animals in all treatment groups are videotaped 24 hours per day starting on Day −7 and continuing through the end of the study to observe feeding behavior including number of meals per day and average duration of feeding per meal.

The primary endpoint will be change in weekly individual animal bodyweights over the course of the study, and these will be summarized and compared to treatment groups. Secondary endpoints will be:

1) Body Composition: Results of individual animal DEXA scans including the percentages of lean and adipose tissue will be summarized over the course of the study; and 2) Feed Consumption/Feeding Behavior: Average daily feed consumption for individual animals in Treatments 1 and 2 will be summarized for each animal.

Videotapes recording the feeding behavior of individual animals will be observed to determine the number of meals and duration of meals each animal consumes prior to the initiation of treatment and following the initiation of treatment.

Results of the impact on body weights are provided in the following table.

TABLE 4

| Group | Weight Loss (kg) |
|---|---|
| Group 1 - control | 0.2 (1.3%) |
| Group 2 - treated | 2.2 (16.1%)[A] |
| Group 3 - treated | 2.1 (14.9%)[B] |

[A]p = 0.001;
[B]p = 0.002.

These results indicate that the groups treated with compound of Example 1 lost more weight as compared to the control group.

The impact on body composition is provided in the following table

TABLE 5

| Group | BCS | DEXA Fat | DEXA Lean |
|---|---|---|---|
| Group 1 - control | 6.8/6.8 | −8.1% | +3.1% |
| Group 2 - treated | 6.8/5.0[A] | −40.2%[C] | −3.7% |
| Group 3 - treated | 7.2/5.5[B] | −36.6[D] | −1.7% |

[A]p = 0.006;
[B]p = 0.049;
[C]p = 0.022;
[D]p = 0.038.

These results indicate that the groups treated with compound of Example 1 had a reduction in body condition scores associated with a preferential decrease in the percentage of adipose tissue and no significant impact on the percentage of tissue as compared to the control group.

The impact on feed consumption and behavior is provided in the following table.

TABLE 6

| Group | Feed Consumed (gm) | Avg. Meals/Day | Avg. Feeding Time/Day |
|---|---|---|---|
| Group 1 | 257.6 | 5/4 | 24/20 |
| Group 2 | 157.4 | 5/4 | 23/15 |
| Group 3 | 184.9 | 5/4 | 32/19 |

These results indicate that the groups treated with compound of Example consumed less food as compared to the control group and the reduction in food intake was associated with reduced time spent eating as opposed to the number of meals consumed per day.

The invention claimed is:

1. A method of treating obesity in a companion animal comprising administering to the companion animal in need thereof an effective amount of a compound, the effective amount is in a range of 0.3 mg/kg to 1.2 mg/kg for at least once a week for five weeks, the compound comprises a polypeptide of SEQ ID NO: 1 and a polyethylene glycol (PEG) moiety, wherein the PEG moiety is covalently attached to a para-acetyl-phenylalanine (pAF) at residue 112 of the polypeptide of SEQ ID NO: 1.

2. The method of treating obesity in a companion animal of claim 1, wherein said PEG moiety is α-methyl-ω-amimooxyethylcarbamyl, polyoxyethylene.

3. The method of treating obesity in the companion animal of claim 1, wherein the compound comprises one or more carriers, diluents or excipients.

4. The method of treating obesity in the companion of claim 3, wherein the compound is in a composition comprising phosphate buffered saline and trehalose.

5. The method of treating obesity in the companion animal of claim 1, wherein the compound is administered subcutaneously.

* * * * *

UNITED STATES PATENT AND TRADEMARK OFFICE
CERTIFICATE OF CORRECTION

PATENT NO. : 10,105,447 B2
APPLICATION NO. : 14/765931
DATED : October 23, 2018
INVENTOR(S) : Michael Bledsoe et al.

Page 1 of 1

It is certified that error appears in the above-identified patent and that said Letters Patent is hereby corrected as shown below:

On the Title Page

Column 2 (Item (56), Other Publications), Line 12: After "Examination" insert -- Search --.

In the Claims

Column 9, Line 63-64: In Claim 2, delete "amimooxyethylcarbamyl," and insert -- aminooxyethylcarbamyl, --, therefor.

Signed and Sealed this
Twenty-third Day of April, 2019

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (112)..(112)
<223> OTHER INFORMATION: Para-acetyl-phenylalanine (pAF)
```

```
<400> SEQUENCE: 1

Met Val Pro Ile Arg Lys Val Gln Asp Asp Thr Lys Thr Leu Ile Lys
1               5                   10                  15

Thr Ile Val Ala Arg Ile Asn Asp Ile Ser His Thr Gln Ser Val Ser
            20                  25                  30

Ser Lys Gln Arg Val Ala Gly Leu Asp Phe Ile Pro Gly Leu Gln Pro
        35                  40                  45

Val Leu Ser Leu Ser Arg Met Asp Gln Thr Leu Ala Ile Tyr Gln Gln
    50                  55                  60

Ile Leu Asn Ser Leu His Ser Arg Asn Val Val Gln Ile Ser Asn Asp
65                  70                  75                  80

Leu Glu Asn Leu Arg Asp Leu Leu His Leu Leu Ala Ser Ser Lys Ser
                85                  90                  95

Cys Pro Leu Pro Arg Ala Arg Gly Leu Glu Thr Phe Glu Ser Leu Xaa
                100                 105                 110

Gly Val Leu Glu Ala Ser Leu Tyr Ser Thr Glu Val Val Ala Leu Asn
            115                 120                 125

Arg Leu Gln Ala Ala Leu Gln Asp Met Leu Arg Arg Leu Asp Leu Ser
            130                 135                 140

Pro Gly Cys
145

<210> SEQ ID NO 2
<211> LENGTH: 441
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
atggttccaa ttcgaaaggt tcaagatgat acgaagacac tgatcaagac tatcgtggcg      60
cgcatcaacg atatttcgca tacccagtca gtctcgtcga acaacgtgt ggctggctta     120 gattttattc cagggctgca accggtactg tctctgagcc gtatggacca aactctggcc    180
atctaccagc aaatccttaa ctctctgcat tctcgcaatg tggtgcaaat ctcgaacgat    240
cttgagaact gcgtgacct gttacatctg ttagcctcaa gcaaatcatg cccgctgccg    300
cgtgcacgtg gccttgaaac gtttgaaagt ttgtagggtg tcttggaagc gagtctttat    360
tccaccgaag tcgtcgccct gaaccgcctg caggccgcac ttcaagacat gcttcgccgt    420
ctggatctca gtccgggttg c                                              441
```